United States Patent [19]
Lee-Own et al.

[11] Patent Number: 6,087,185
[45] Date of Patent: *Jul. 11, 2000

[54] INTEGRATED PACKAGING HOLDER DEVICE FOR IMMUNOCHROMATOGRAPHIC ASSAYS IN FLOW-THROUGH OR DIPSTICK FORMATS

[75] Inventors: F. Victor Lee-Own, Bedminster; Judith Fitzpatrick, Tenafly, both of N.J.

[73] Assignee: Serex, Inc., Maywood, N.J.

[*] Notice: This patent is subject to a terminal disclaimer.

[21] Appl. No.: 08/971,250

[22] Filed: Nov. 17, 1997

Related U.S. Application Data

[63] Continuation of application No. 08/539,170, Oct. 4, 1995, abandoned, which is a continuation of application No. 08/047,156, Apr. 13, 1993, Pat. No. 5,500,375.

[51] Int. Cl.[7] ............... G01N 33/537; G01N 33/543
[52] U.S. Cl. .............. 436/514; 422/56; 422/57; 422/58; 435/7.92; 435/970; 435/287.2; 436/518; 436/527; 436/528; 436/530
[58] Field of Search ............... 422/56, 57, 58; 435/7.92, 970, 287.2; 436/514, 518, 527, 528, 530

[56] References Cited

U.S. PATENT DOCUMENTS

| | | |
|---|---|---|
| 4,806,312 | 2/1989 | Greenquist . |
| 4,857,453 | 8/1989 | Ullman et al. . |
| 4,861,711 | 8/1989 | Friesen et al. . |
| 4,981,786 | 1/1991 | Dafforn et al. . |
| 4,999,163 | 3/1991 | Lennon et al. . |
| 5,006,464 | 4/1991 | Chu et al. . |
| 5,030,558 | 7/1991 | Litman et al. . |
| 5,114,673 | 5/1992 | Berger et al. . |
| 5,137,808 | 8/1992 | Ullman et al. . |
| 5,156,952 | 10/1992 | Litman et al. . |
| 5,238,652 | 8/1993 | Sun et al. . |
| 5,330,715 | 7/1994 | Blake et al. . |
| 5,409,664 | 4/1995 | Allen . |
| 5,500,375 | 3/1996 | Lee-Own et al. .............. 436/514 |
| 5,712,172 | 1/1998 | Huang et al. ................. 436/518 |

FOREIGN PATENT DOCUMENTS

| | | |
|---|---|---|
| 0 271 204 A2 | 6/1988 | European Pat. Off. . |
| 0 362 809 A2 | 4/1990 | European Pat. Off. . |
| 2 204 398 | 11/1988 | United Kingdom . |

*Primary Examiner*—David Saunders
*Attorney, Agent, or Firm*—Arnall Golden & Gregory, LLP

[57] ABSTRACT

The prevent invention relates to an integrated package-holder assay devices for detecting the presence of analyte in a sample. The device serves the dual roles of supporting and protecting an immunochromatographic assay. The device is compatible with any immunochromatographic assay format. The assay can be performed in a single apparatus for use in a laboratory or a field setting. In a specific example, the assay device is a nylon membrane formatted for an immunochromatographic assay for cotinine sealed between transparent adhesive tape and a stiff plastic strip. White tape placed over the plastic strip defined a window for observing the assay results.

20 Claims, 4 Drawing Sheets

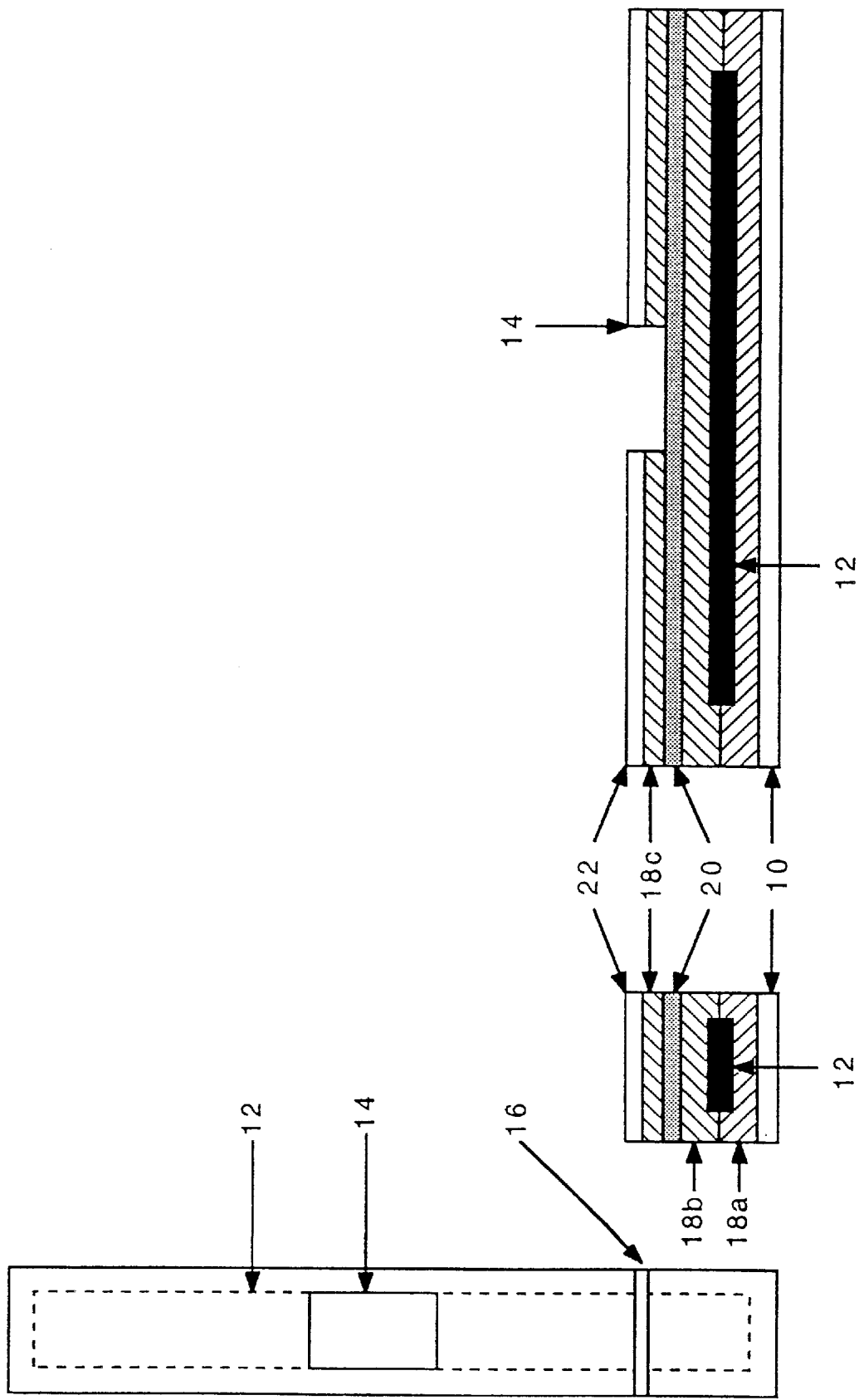

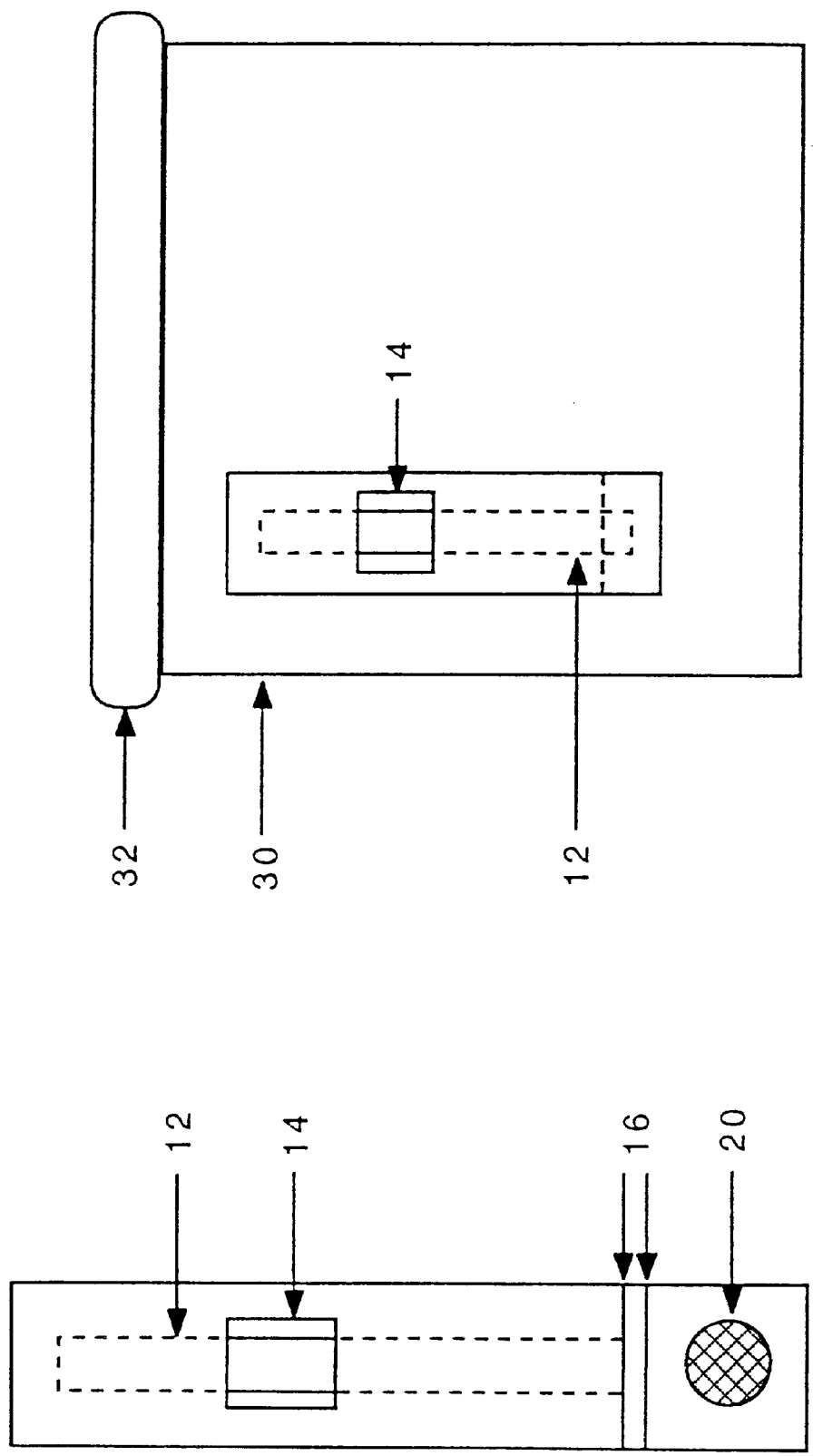

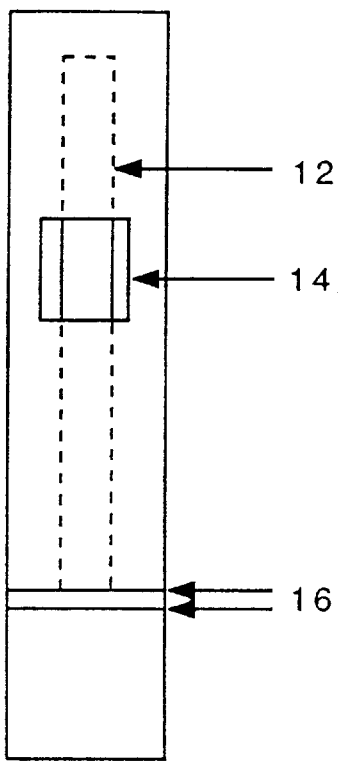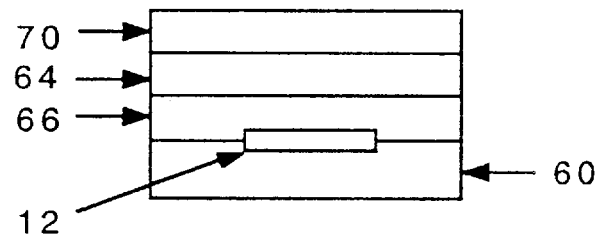
FIG. 10
FIG. 11

INTEGRATED PACKAGING HOLDER DEVICE FOR IMMUNOCHROMATOGRAPHIC ASSAYS IN FLOW-THROUGH OR DIPSTICK FORMATS

This is a continuation of application Ser. No. 08/539,170, filed on Oct. 4, 1995 now abandoned, which is a continuation of application Ser. No. 08/047,156, filed on Apr. 13, 1993, now U.S. Pat. No. 5,500,375.

1. FIELD OF THE INVENTION

The prevent invention relates to assay devices for detecting the presence of analyte in a sample. The assay can be performed in a single apparatus for use in a laboratory or a field setting.

2. BACKGROUND OF THE INVENTION

2.1. Immunochromatographic Assay Devices

Immunochromatographic assays using a membrane as a solid support in a dipstick or flow-through device are now established for use in the clinical laboratory and for alternative, i.e., non-laboratory, site testing. Assays using this type of format are available for drugs of abuse (cocaine, cannabinoid, amphetamines, opiates, PCP), pregnancy and fertility (hCG and hLH, respectively), and infectious diseases (chlamydia, Strep A, infectious mononucleosis (IM)).

The usual presentation for an immunochromatographic assay device is a membrane (cellulosic or non-cellulosic) enclosed in a plastic holder. This device is further packaged singly or in bulk in a sealed foil or plastic pouch, which acts as an environmental control. Package integrity is essential for extended stability of the device at room temperature.

The plastic holder keeps the membrane in a suitable configuration in order to ensure correct functioning of the entire device. There are usually 1–3 windows in the holder. There is always a test window which serves to allow observation of the result. The test window may also allow for viewing of a control reaction, e.g., to confirm adequate performance of the test; alternatively, the control window may be separate from the result window. Additionally there may be a third window that allows application of the liquid sample to the membrane, either by direct placement of the device in the sample (allowing contact of the sample at the open window), or by application of the sample with a dropper at the window. The plastic holder also usually holds the membrane in contact with pads (cellulosic or non-cellulosic) which serve as wicks. Usually there is an applicator pad at the sample application window or at the site where the sample is applied, and a pad at the opposite end of the membrane. The plastic holder keeps the pad(s) in contact with the membrane, thus providing a continuum for wicking of sample from the applicator up through the membrane and from the application pad to the top pad.

There are many variations of the basic structure of assay devices. For example, Litman et al. (U.S. Pat. Nos. 5,156,952 and No. 5,030,558) describe an assay method and device for determining the presence of a minimum amount of an analyte in a sample. Ullman et al. (U.S. Pat. Nos. 5,137,808 and 4,857,453) describe an device to house an assay membrane that includes self-contained liquid reagents to aid sample flow. Dafforn et al. (U.S. Pat. No. 4,981,768) describes a device with ports for applying sample and extra liquid. Assay devices are also described by Corti et al. (European Patent Application No. 89118378.2), Greenquist et al. (U.S. Pat. No. 4,806,312) and Berger et al. (U.S. Pat. No. 5,114,673).

The plastic device containing the membrane and pads is usually packaged in a sealed foil or plastic pouch with or without desiccant. The outer packaging pouch is essential as an environmental control, particularly to limit exposure of the membrane strip to the external environment and to ensure integrity of the test. Low humidity within the package is important essential for extended room temperature stability of the device, thus a desiccant is usually present. The addition of a moisture indicator inside the sealed package, or integral to the device, insures integrity of the device before use.

The usual test procedure involves opening the outer packaging and removal of the plastic device, application of the sample at the sample window (by dipping the device into the sample, or by dropping the sample onto the sample window), waiting the recommended time for running the assay, and checking the result window for a positive or negative result and the control window to determine whether the test proceeded correctly.

The packaging required for test devices present certain drawbacks. For example, if the devices are packaged in bulk, any breach of the packaging, whether by an accidental tear or to retrieve a device for a test, will limit the shelf life of the devices. Individual packaging of each test device is expensive, and produces additional solid waste for disposal.

Thus, it is the object of the present invention to provide an integrated packaging-holder immunochromatographic assay device. It is a further object to provide a device that eliminates the need for a separate plastic holder and outer packaging.

2.2. Detection of Analyte in Competitive Assays

Competitive assays, which are the rule for small analytes, yield a "negative" signal in the presence of an analyte and a "positive" signal in the absence of analyte. Thus, the presence of analyte is inversely proportional to the presence of a signal. This inverse relationship between signal and the presence of an analyte can potentially have serious consequences when observed by laymen. This inverse correlation is confusing and illogical and limits the usefulness of such tests in the field.

In a standard competitive immunochromatographic device, the labeled reagent, which can be either analyte or receptor labeled with a marker, migrates to a trap, which is membrane coated with either receptor (if the labeled reagent is analyte) or analyte (if the labeled reagent is receptor). If the sample contains analyte it binds to the receptor (either mobile or stationary phase) and the marker is not captured by the trap, yielding a "negative" signal. If the sample does not contain the analyte, the marker is captured by the trap and a spot appears, i.e., a "positive" signal. So in a standard competitive assay a negative result has a positive signal.

Thus, it is a further object of the present invention to provide an assay device that gives an apparent "positive" signal in a competitive immunoassay format when the sample contains analyte, and an apparent "negative" signal when the sample lacks analyte.

Other methods have been proposed for getting a positive signal to correlate with the presence of a small analyte in a sample. However, these require applying extra traps, that have been accurately titered, to the assay membrane. Such methods, while providing useful assay devices, increase the complexity of manufacture, and therefore the cost, of the device.

3. SUMMARY OF THE INVENTION

The present invention relates to an integrated packaging-holder laminate for flow-through and dipstick immunochromatographic assays. The device comprises means for conducting an immunochromatographic assay, e.g., a membrane onto which the assay reagents have been previously impregnated, totally surrounded by means for sealing the immunochromatographic assay means in a substantially air-tight and a substantially fluid-tight manner, e.g., mylar, plastic or other suitable support. The sealing means contact and support the assay means, and are adapted to be opened to expose the assay means.

The laminate can be sealed with double sided tape or adhesive film, or any other method such as sonic welding, that will similarly enclose the membrane strip in an air-tight and fluid-tight manner. The laminate thus acts as an integral holder for the membrane as well as a packaging pouch. Configurations include a single strip or multiple strips in one laminate, and a single strip may have capability of running multiple tests simultaneously.

The invention preferably comprises a test-strip membrane enclosed totally by direct contact on all surfaces with the laminating adhesive supplied as double sided tape or adhesive film. The strip is then given support as needed by overlaying with plastic, mylar, or other suitable material on the back (non-viewing) side. The front (viewing side) can be covered with transparent plastic. A further layer of opaque material (white or colored plastic, tape, card, paper, paint, pigment, etc.) is then attached directly over the transparent plastic (front) by adhesive, leaving suitable window(s) for viewing results. The laminate contains the totally enclosed test-strip membrane, which is thus presented in its own dedicated holder/packaging pouch, isolated from the external atmosphere. This eliminates the need for separate packaging (plastic/foil pouch or blister pack) for device.

The invention may be used with any assay format that is compatible with an immunochromatographic assay, e.g., "competitive" and "sandwich" assays.

It is a particular advantage that the immunochromatographic assay device of the invention provides its own packaging material.

It is a further advantage that the assay device does not require extraneous wicks or pads to augment sample migration, nor are extra fluids required for sample migration.

The invention is based on the surprising discovery that an immunochromatographic assay support, such as a nylon strip, that has been sealed in an air-tight and fluid-tight manner, can be used in an immunochromatographic assay.

The present invention further relates to a zone for positively detecting the presence of an analyte in a sample in a competitive immunochromatographic assay on an assay strip. According to the invention, the immunochromatographic assay includes a mobilizable labeled reagent, such that in the presence of a liquid sample the labeled reagent is transported with the sample along the assay strip a detection zone. The detection zone contains label immobilized in an area of the detection zone such that there is a contrast between the label and the membrane strip in the detection zone. In the performance of the assay, a contrasting signal in the detection zone indicates the presence of analyte in the sample and a non-contrasting signal in the detection zone indicates the absence of analyte in the sample.

4. BRIEF DESCRIPTION OF THE DRAWINGS

The device of the invention can be appreciated by the figures, which are schematic drawings and are not drawn to scale.

FIG. 1 is a top view of a device of the present invention.

FIG. 2 is a cross-section end view of the device in FIG. 1.

FIG. 3 is a cross section side view of the device in FIG. 1.

FIG. 4 is a top view of another embodiment of a device of the present invention.

FIG. 5 is a side view of yet another embodiment of the device of the present invention.

FIG. 10 is a top view of specific embodiment of another device of the invention.

FIG. 11 is a cutaway end view of the device shown in FIG. 10.

5. DETAILED DESCRIPTION OF THE INVENTION

Figure 6:
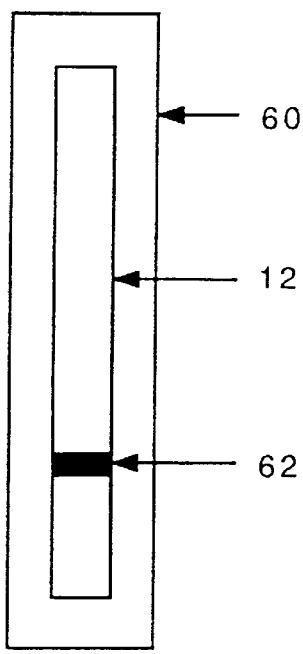
FIG. 6 is a top view of a schematic of a partial construction of a specific embodiment of the invention.

The present invention relates to an immunochromatographic assay device (FIGS. 1, 2 and 3) for detecting the presence of an analyte in a sample. The assay device comprises means for conducting an immunochromatographic assay 12 in contact with and sealed within a substantially air-tight and substantially fluid-tight manner within means for sealing (18a and 18b). The invention further comprises a support means 20, which supports the assay means. The sealing means contact and support the assay means. The sealing means are adapted to be opened by the user to provide access to the assay means, i.e., to apply sample.

The invention further provides a detection system that gives a positive result in a competitive immunoassay format when an analyte of interest is present in a sample.

As used herein, the term "sample" refers to an aqueous liquid sample suspected of containing an analyte of interest. Such samples include but are not limited to blood, plasma, serum, urine, saliva, sweat, effusions, fluid, and materials reconstituted or dissolved in a suitable aqueous solvent, e.g., a buffer solution.

As used herein, the term "analyte" refers to a molecule of interest. Analytes may be any antigen, but small analytes (MW of 100 to 1000 Daltons) are of primary interest. Such analytes include therapeutic drugs and metabolites thereof, illicit drugs and metabolites thereof, steroids, and peptide hormones. Nevertheless, assays may be for larger molecules such as protein hormones, e.g., insulin, or viral antigens, bacterial antigens, serum proteins, antibodies or any antigen of interest where detection of the presence (or absence) of the analyte in a rapid, specific, sensitive assay is desirable.

5.1. Immunochromatographic Assays

The device of the invention comprises means for conducting an immunochromatographic assay ("immunochromatographic assay means"). Many immunochromatographic assay means and formats are known in the art (see Section 2.1, supra), and can be used in the practice of the present invention. Generally, an immunochromatographic assay involves use of a solid phase support for conducting a liquid. As used herein, the term "solid phase means for conducting a liquid" refers to a solid support that allows migration of a liquid therethrough, e.g., via capillary action.

In the practice of the present invention, the solid phase support should behave as a hydrogel. Although not intending to be limited by any particular theory, it is believed that hydrogel materials permit the migration of a liquid sample into the substantially air-tight environment of the device of the invention. A suitable solid phase immunochromatographic assay means is a nylon membrane, which is the preferred solid phase support for this purpose, although any solid phase which permits movement of the sample may be used. Other suitable solid phase supports for include, but are not limited to, coated plastic and coated glass, e.g., such as is used for thin layer chromatography, filters, polymer beads, silica gel, paper, membranes, agarose gel, polyacrylamide gel, gelatin, etc. In a further embodiment, the solid phase support may be impregnated with hydrogel materials such as, but not limited to, proteins (e.g., collagen, gelatin, albumin, etc.), polyethylene glycol, charged or neutral polysaccharides (e.g., hyaluronic acid, xanthates, alginates, guar gum, agarose, etc.) and starches. In another embodiment, adhesive polymers used to seal the immunochromato-graphic assay means can also have hydrogel properties.

The immunochromatographic assay means of the invention will preferably be a membrane strip, more preferably a nylon membrane strip. However, it is contemplated that the immunochromatographic means may be formatted for radial migration of liquid sample, e.g., as on a disk.

The present invention can be used with any assay format adaptable to an immunochromatographic assay. Although not limited by any particular example, Generally, depending on the assay format, the immunochromatographic assay means will contain a mobilizable labeled reagent and a detection zone for detecting the labeled reagent. As use herein, the term "labeled reagent" refers to labeled receptor specific for the analyte of interest, or labeled analyte, and the term "mobilizable" means that the reagent will move along the solid phase support with the liquid sample. The mobilizable labeled reagent is located on the solid phase support so that it can be mobilized by the liquid sample and moved to the detection zone. In a specific embodiment, infra, the labeled reagent is labeled analyte. In a competitive assay format, the detection zone contains a specific binding partner of the labeled reagent immobilized in the detection zone, i.e., analyte if labeled receptor is used, or receptor if labeled analyte is used (see Section 2.2, supra). As pointed out in Section 2.2, supra, there is an inverse correlation between detection of label in the detection zone and the presence of analyte in the sample.

In a sandwich immunoassay format, one receptor is labeled, and another receptor, which does not compete with the first receptor for binding to analyte, is immobilized in the detection zone. When analyte is present, it will bind both labeled receptor and immobilized receptor, thus localizing the label in the detection zone. In this case, a signal directly correlates with the presence of analyte.

Preferably, the immunochromatographic assay means includes a control to indicate that the assay has proceeded correctly. The control can be a specific binding spot more distal from the sample application point on the solid phase support than the detection zone that will bind to labeled reagent in the presence or absence of analyte, thus indicating that the mobilizable receptor has migrated a sufficient distance with the liquid sample to give a meaningful result.

The term "receptor" refers to a molecule that can specifically bind to analyte. Suitable receptors for use in assays of the invention include antibodies, cell surface receptors (or a fragment of a cell surface receptor that contains the binding site of analyte and ligand), enzymes (or the substrate binding site of an enzyme), or any other molecule or macromolecule capable of specifically binding to and forming a complex with a ligand and complex with an analyte. Antibodies and cell surface receptors are preferred, with antibodies more preferred. In a preferred embodiment, receptor is generated or selected to be specific for the most unique epitope on the analyte.

Suitable labels include enzymes, fluorophores, chromophores, radioisotopes, dyes, colloidal gold, latex particles, and chemiluminescent agents. When a control marker is employed, the same or different labels may be used for the receptor and control marker. In a specific embodiment, infra, the label is a colored latex particle.

5.2. Sealing and Support of the Device

The device also comprises a means for sealing the immunochromatographic assay means ("sealing means"), also referred to as a sealing member. As used herein, the terms "sealing means" and "sealing member" refer to a material that can be used to seal the immunochromatographic assay means in a substantially air-tight and a substantially liquid-tight manner. The sealing means should also be substantially non-wettable, i.e., it does not absorb significant amounts of water. According to the present invention, material useful as sealing means includes, but is not limited to, adhesive tape, plastic, mylar and the like. In one embodiment, the sealing means are sealed with an adhesive. In another embodiment, the sealing means are sealed with a sonic weld. Although not intending to be limited by a particular theory, it is believed that sealing with an adhesive confers non-rigidity to the device, allowing migration of air into interstitial spaces of the adhesive or slight separation of the sealing means to allow for the movement of liquid in the solid phase support.

The device also comprises a means for supporting the device ("support means"), also referred to as a support member. As used herein, the terms "support means" and "support member" refer to a material which can act to reinforce the solid phase means for conducting a liquid, i.e., to buttress or brace a membrane strip. The support means is selected from a material that can be attached to the sealing means, e.g., via an adhesive. In a specific embodiment, the support means can also act as sealing means. Materials for use as support means include, but are not limited to, glass, plastic, mylar and the like. In a preferred embodiment, the support means is transparent plastic that is stiff enough to support a nylon membrane. Alternatively, a relatively non-stiff material can have suitable stiffeners attached thereto.

In the device, the solid phase means for conducting a liquid is laminated between the sealing means and the support means. Thus, the dimensions of both the support means and the sealing means are larger that the dimensions of the immunochromatographic assay means.

Preferably the device defines a transparent window aligned with the test zone for viewing the assay results.

The invention further contemplates sealing more than one immunochromatographic assay means, e.g., membrane strips, in a single device, to allow for multiple assays.

5.3. Preferred Embodiments of the Invention

Referring now to FIGS. 1, 2 and 3, in a specific embodiment, a membrane strip 12, onto which the assay reagents have been previously impregnated and stabilized, is attached directly to a sealing member 10 (plastic, mylar or other suitable material) by means of any lamination technique such as double sided tape or adhesive film 18*a*, or sonic welding. A further application of double sided tape or adhesive film 18*b* is then applied to the remaining exposed membrane surface, followed by a layer of stiff transparent plastic sheet 20 to totally enclose the membrane strip. Alternatively, the stiff transparent plastic sheet 20 can be sealed to the sealing member 10 by sonic welding.

In a further embodiment, the transparent plastic sheet 20 can then be overlaid indirectly with double sided tape or adhesive film 18*c* followed by white or colored tape or plastic 22 (or alternatively directly with white or colored adhesive backed tape or plastic 22) leaving an appropriate window 14 (or windows) to allow for viewing of the test result and control reaction. Alternatively, the transparent plastic sheet 20 can be painted, stained, or colored to define a window 14.

Fabricated as described above, the membrane strip is totally enclosed within non-wettable sheets in packaging which serves the duplicate function of membrane holder and moisture barrier pouch.

The assay is carried out simply by exposing the end of the membrane strip, e.g., by cutting the laminate or by pealing off a protective cover. Preferably, cut marks 16 are indicated on the device. This exposed membrane is then dipped into the sample (which enters through the exposed end) and migrates up the membrane. Alternatively the device can just be immersed in the sample (for example, a full urine collection vessel) and the sample will enter through the exposed end of the membrane (the only channel of access available) and migrate up. In another embodiment, the sample can be applied to the exposed membrane. The result is read as the presence or absence of label in the detection zone. In a preferred aspect, the label is observed through the viewing window 14. Moreover, because the device is an integral arrangement of the immunochromatographic assay totally enclosed in the packaging, it can be removed from the sample, dried off, preferably resealed (e.g., with adhesive tape) and stored conveniently as a permanent record.

Selection of membrane and lamination method can be controlled so that such devices have controlled pore sizes and effectively eliminate particles above a certain size, such as red-blood cells, making such a device useful for whole blood.

The device of the present invention provides for enclosing any immunochromatographic assay means, e.g., a membrane strip, such as used in immunochromatographic assays in dipstick or flow-through format for pregnancy (hCG), fertility (hLH), infectious mononucleosis (IN), Strep A, chlamydia, and drugs of abuse, using lamination so that the membrane is contacted on all sides and totally enclosed. The laminate can be then be completed with plastic, mylar or any other material as required for rigidity and or cosmetic appearance. As pointed out above, the membrane is thus held in a device that acts as an integral holder and packaging pouch.

In another embodiment, a membrane such as that described in U.S. patent application Ser. No. 07/737,091, filed Jul. 29, 1991 and now U.S. Pat. No. 5,451,504 can be used in the device.

The device of the present invention provides good control of liquid sample migration, since the volume of sample entering the device is limited by the physical dimensions of the enclosed test-strip membrane. The migration of the sample is strictly controlled by the physical limitations imposed by the confinement of the test-strip membrane in the laminate. The volume of sample that enters is controlled by the area of membrane used.

In one preferred embodiment the laminate is assembled from test-strip membranes and sheets of materials (adhesive films, tapes, transparent plastic sheets, etc.) then the final laminate is die-cut at the required dimensions. This eliminates the cost involved in using precut or molded components and the accuracy that would be involved in the assembly of individual components into a laminate.

Referring now to FIG. 4, in another preferred embodiment a colored indicator strip 24 that can indicate the presence of moisture levels (blue for low humidity, pink for high humidity), is incorporated into the device. Suitable indicator strips are sold by Multiform Desiccants. Alternatively, a suitable moisture indicator can be impregnated in a part of the solid phase support that is not intended to contact sample. The colored area is given its own viewing window at the top or bottom of the laminate. The indicator serves as a confirmation of package integrity. When the colored area is pink—indicating high moisture—the laminate integrity has been compromised and the test should not be used. Satisfactory package integrity is indicated by the colored area remaining blue.

Referring now to FIG. 5, in yet another embodiment the laminate is incorporated into a sample collection vessel 30 such as a urine collection vessel, thus allowing immediate specimen testing in the collection container. The collection vessel should be transparent to allow for viewing of the result. The device is attached to the inside wall of the collection vessel by adhesive film, double sided tape, or a sonic weld. In this embodiment the laminate can be precut, with the test-strip membrane 12 exposed (i.e., as if the test is ready to run). The collection vessel 30 is then sealed (cap 32 screwed on, etc.) to provide the package integrity. Alternatively, the device may include a removable adhesive strip so that the membrane strip remains sealed within the laminate until the test is ready to run. In this case, the adhesive strip is removed prior to adding the sample. The test runs automatically when the sample is collected in the vessel. The amount of sample collected need only be sufficient to be above the level at which the test-strip membrane is exposed.

5.4. Preferred Detection Zones of the Invention

In addition to the integral immunochromatographic assay device, the present invention provides an advantageous detection zone for a competitive assay format. The detection zone of the invention gives a positive signal when analyte is present in the sample, and a negative signal when analyte is not present in the sample, in contrast to standard competitive assay techniques (see Section 2.2, supra). The immunochromatographic assay includes a mobilizable labeled reagent, such that in the presence of a liquid sample the labeled reagent is transported with the sample along the assay strip a detection zone. The label has been immobilized in part, but not all, of the detection zone such that there is a contrast between the label and the membrane strip in the detection zone. The detection zone also includes a specific binding partner of the labeled reagent, as described above. However, when labeled reagent binds to the specific binding partner in the detection zone, i.e., in the absence of analyte in the sample, the contrast between the label in the detection zone and the membrane strip is lost. When the labeled reagent does not bind to the detection zone, i.e., in the presence of analyte, the contrasting signal remains. Thus, a contrasting signal in the detection zone indicates the presence of analyte in the sample and a non-contrasting signal in the detection zone indicates the absence of analyte in the sample. In this way, the signal directly correlates with the presence of analyte in the sample.

In another embodiment, the detection zone contains specific binding partner of the labeled reagent in one section, and a non-specific, i.e., control, binding partner of the labeled reagent (or alternatively a binding partner of a control labeled reagent) in another part. In the presence of analyte, the control reagent will bind in the control area of the detection zone, while the labeled reagent will not, thus producing a contrast between labeled and unlabeled areas of the detection zone, indicating (1) a "positive" result and (2) that the assay ran correctly. In the absence of analyte, the entire detection zone will be labeled, indicating (1) a "negative" result and (2) that the assay ran correctly. If the detection zone is not labeled at all, the assay failed to run.

It can be readily appreciated that the contrasting areas in the detection zone can be arranged in shapes, such as "+" signs or letters.

As can be appreciated by one of ordinary skill in the art, any label system commonly used for immunochromatographic assays can be used according to the present invention.

The present invention will be made more clear by the following example, which is intended to be exemplary of the invention and not limiting.

6. EXAMPLE: DETECTION OF COTININE IN A SAMPLE

6.1. Materials and Method

Preparation of cotinine coated particles. Blue dyed latex (0.318 $\mu$m diameter, Seradyn, Ind.) was coated with a solution of cotinine chemically linked to bovine gamma globulin (cotinine-BGG) overnight at room temperature in 0.05 M phosphate buffer, pH 7.2–7.5. The final concentration of blue latex was 0.25% and that of the cotinine-BGG was 3 $\mu$g/ml. The particles were washed twice with 5 mg/ml BSA in phosphate buffer, pH 7.2–7.5, and the coated latex solution was suspended in phosphate buffer containing 5 mg/ml BSA.

Rabbit antibody to cotinine. Rabbit antibody raised against a cotinine derivative were prepared against a trans-4-hydroxycotinine-KLH conjugate using standard procedures, as described in U.S. application Ser. No. 07/737, 526, filed Jul. 29, 1991 (now abandoned) and International Patent Publication No. WO 93/03367, published Feb. 18, 1993. The antibody was affinity purified batchwise by affinity chromatography on Sepharose-cotinine. The affinity purified material was diluted in 0.5 M sodium carbonate, pH 9.5, at a concentration of 350 $\mu$g/ml.

Control antibody. Rabbit anti-sheep antibody (Jackson Immunoresearch Labs) was diluted to 1.2 mg/ml in 0.5 M sodium carbonate, pH 9.3.

Preparation of the test-strip membrane. Nylon membranes (Biodyne A, 5 $\mu$m pore size, Pall Biomembranes, N.Y.) were cut into 7×10 cm sheets. Affinity purified rabbit anticotinine antibody and the control antibody were applied to the sheet of nylon as lines (20 $\mu$l per line, 8 cm long at the rate of 2.5 $\mu$l/cm). The line widths were 2 cm and 2.5 cm, respectively, from the bottom end of the sheet, parallel to the 10 cm side. The application was performed using a mechanized air-brush applicator with 25–75 psi nitrogen. The sheets were then allowed to air dry at room temperature for 1 h followed by 30 minutes in an incubator at 37° C. The sheets were then soaked, with agitation, in an aqueous solution of 0.5% casein, 5% sucrose, 0.1% TRITON X-100, 0.05 M Tris, 0.003 M $MgCl_2$, 0.9% NaCl, 0.02% $NaN_3$, pH 8.0, for 30 minutes. The sheets were air dried for at least 4 h at room temperature.

Blue latex coated with cotinine-BGG diluted to 0.25% in 20% sucrose was applied to the sheet of nylon as zones adjacent and parallel to the affinity purified rabbit anti-cotinine line. Each zone was approximately 0.3×0.5 cm with approximately a 1.5 mm gap between each zone. The gaps were visible. The zone was applied about 1.5 cm from the bottom end of the sheet. The application was performed using a mechanized air-brush applicator with 25–75 psi nitrogen. The sheets were then allowed to air dry at room temperature.

The 7×10 cm sheet was cut into strips 0.5×7 cm with each strip having a visible blue latex zone and an affinity purified anti-cotinine line and a control antibody zone.

Assembly of test-strip membrane in its integrated holder/packaging pouch.

Figure 7:
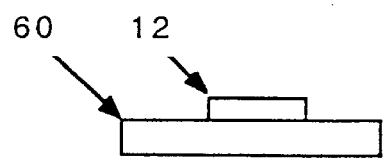
FIG. 7 is a cutaway end view of the device shown in FIG. 6.

(a) Referring to FIGS. 6 and 7, a test-strip membrane 12 was placed onto a piece (2×8 cm) of Arclad 7148 double sided-tape 60 (Adhesives Research, Pa.). The uncoated surface of the membrane (side not impregnated with the coated blue latex and antibodies) was attached to the exposed surface of the tape and the membrane was located centrally within the piece of tape.

Membrane 12 was placed on tape 60 with the strip 62 of blue latex is positioned approximately as shown in FIG. 6.

Figure 8:
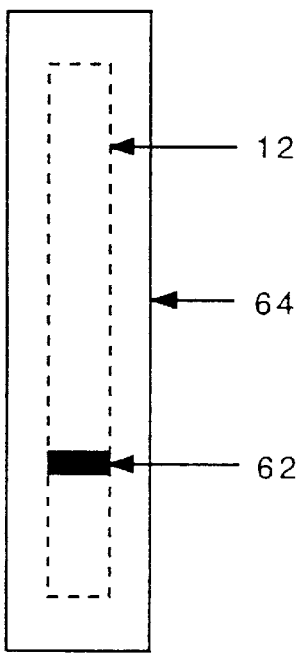
FIG. 8 is a top view of the completed device shown in FIG. 6.
Figure 9:
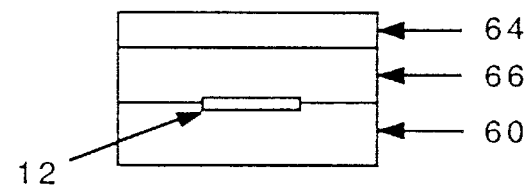
FIG. 9 is a cutaway end view of the device shown in FIG. 8.

(b) Referring now to FIGS. 8 and 9, the membrane strip 12 was totally enclosed by covering the exposed surfaces of membrane and adhesive with a piece (2×8 cm) of Arclad 7530 adhesive film 66 (Adhesives Research, Pa.). The covering over the second adhesive surface of the 7530 was removed and the exposed surface (the top surface) was covered with transparent plastic film 64, i.e., the support member. The adhesive film and plastic film were firmly pressed on all sides to allow complete contact of all adhesive surfaces and sealing of the membrane totally within the assembly.

(c) Referring now to FIGS. 10 and 11, the transparent plastic top surface was then covered by white or colored tape or plastic 70 (directly with adhesive backed material, although the same effect could be achieved indirectly with double sided tape or adhesive film followed by white or colored tape or plastic) leaving an appropriate window 14 (or windows) above the affinity purified anti-cotinine line and the control antibody line on the membrane strip 12 to allow for viewing of the test result and control reaction. Additionally, the bottom end of the laminate was marked with 2 lines 16, just below the strip 62 of coated blue latex. The space between the two lines was cut in order to expose the test-strip membrane 12 to sample for performing a test. The whole assembly, test-strip membrane in its integrated holder packaging pouch, is the device for an assay for cotinine.

Assay for Cotinine. The test kit was prepared for use by cutting the device at the bottom where indicated by the two marker lines. This exposed the end of the test-strip membrane.

The device was put into sample such that the cut end of the device was in contact with the sample. The device was left to stand in the sample for 10 minutes, after which time the results were read. Samples were urine samples containing known amounts of cotinine.

6.2. Results

Sixty tests were performed with urine samples having known cotinine concentrations received from the Centers for Disease Control (CDC). The results of assays using the device ("Detection with the Device") are shown below in Table 1 and compared to the cotinine concentrations of the samples and the positive cut-off value of 100 ng/ml proposed by the CDC.

TABLE 1

Results of Tests For Cotinine in Urine Samples

| Sample # | Cotinine Conc. ng./ml in the sample | Detection based on the CDC cut-off 100 ng/ml* | Detection with the Device |
|---|---|---|---|
| 1. | 3080 | + | + |
| 2. | 1360 | + | + |
| 3. | 2860 | + | + |
| 4. | 1250 | + | + |
| 5. | 2450 | + | + |
| 6. | 37 | − | − |
| 7. | 194 | + | − |
| 8. | 23 | − | − |
| 9. | 6.9 | − | − |
| 10. | 590 | + | − |
| 11. | 102 | + | − |
| 12. | 25.5 | − | − |
| 13. | 540 | + | + |
| 14. | 6460 | + | + |
| 15. | 32.2 | − | − |
| 16. | 17.5 | − | − |
| 17. | 520 | + | + |
| 18. | 50.5 | − | − |
| 19. | 56.2 | − | − |
| 20. | 24.2 | − | − |
| 21. | 2310 | + | − |
| 22. | 1060 | + | − |
| 23. | 15.3 | − | − |
| 24. | 230 | + | + |
| 25. | 276 | + | + |
| 26. | 122 | + | + |
| 27. | 122 | + | − |
| 28. | 320 | + | + |
| 29. | 510 | + | + |
| 30. | 9.5 | − | − |
| 31. | 590 | + | + |
| 32. | 960 | + | + |
| 33. | 1450 | + | + |
| 34. | 890 | + | + |
| 35. | 27.3 | − | − |
| 36. | 13.8 | − | − |
| 37. | 232 | + | − |
| 38. | 272 | + | + |
| 39. | 590 | + | + |
| 40. | 26.1 | − | − |
| 41. | 55.2 | − | − |
| 42. | 326 | + | + |
| 43. | 106 | + | + |
| 44. | 780 | + | + |
| 45. | 2070 | + | + |
| 46. | 510 | + | + |
| 47. | 670 | + | + |
| 48. | 54 | − | − |
| 49. | 67.8 | − | − |
| 50. | 570 | + | − |
| 51. | 1500 | + | + |
| 52. | 154 | + | + |
| 53. | 200 | + | − |
| 54. | 164 | + | + |
| 55. | 176 | + | − |
| 56. | 1500 | + | − |
| 57. | 7470 | + | + |

TABLE 1-continued

Results of Tests For Cotinine in Urine Samples

| Sample # | Cotinine Conc. ng/ml in the sample | Detection based on the CDC cut-off 100 ng/ml* | Detection with the Device |
|---|---|---|---|
| 58. | 1860 | + | + |
| 59. | 5860 | + | + |
| 60. | 238 | + | − |

*The samples were graded as positive or negative by the CDC based on the detected concentration of cotinine; negative <100 ng/ml., positive >100 ng/ml.

Table 2 summarized the results of Table 1. The number of samples that registered as positive for cotinine under the CDC criteria and using the device are in the "+,+" square (32); the number of samples that registered positive using the device of the invention, but that were negative according to the CDC criteria are shown in the "+,−" square (0); the number of samples that registered as negative using the device, but that are positive according to the CDC criteria are in the "−,+" square (11); and the number of samples that registered negative using the device and that are negative according to the CDC criteria are shown in the "−,−" square.

TABLE 2

SUMMARY OF COTININE ASSAY RESULTS

|  |  | Result, cut-off 100 ng/ml cotinine | |
|---|---|---|---|
|  |  | + | − |
| Device | + | 32 | 0 |
|  | − | 11 | 17 |

The following observations about accuracy (the percentage of correct assay results using the device), sensitivity (the percentage of correct positive results using the device) and specificity (the percentage of correct negative results using the device) are available from the data in Table 2. The overall accuracy of the assay using the device of the invention to test samples of known cotinine concentration, in which the cut-off for a positive result is 100 ng/ml, is 81.6% (49 out of 60). This value is calculated by adding all of the "+,+" and "−,−" values and dividing by the total number of tests. The sensitivity or the assay using the device, which is calculated from the number of samples that registered positive divided by the total number of positive samples according to the CDC criteria, was 74.4% (32 out of 43). The specificity of the device, which is calculated from the number of samples that registered negative divided by the total number of negative samples according to the CDC criteria, was 100% (17/17).

The results clearly show the present invention is able to detect cotinine in the urine samples.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. An immunochromatographic assay device comprising: means for conducting an immunochromatographic assay to detect the presence of an analyte in a sample, wherein the assay means defines a detection zone and absorbs sample; and laminate means for sealing the assays means in a substantially air-tight and a substantially fluid-tight manner, the laminate sealing means contacting and supporting the assay means.

2. The device according to claim 1, in which the laminate sealing means is adapted to be opened by cutting the sealing means.

3. The device according to claim 1, wherein the laminate sealing means defines a transparent window aligned with the detection zone for viewing the assay results.

4. The device according to claim 1, further comprising stiffening means joined to the sealing means for stiffening the device.

5. The device according to claim 4, wherein the sealing means and the stiffening means are substantially transparent and the device further comprises a substantially non-transparent layer joined to the stiffening means to define a window for viewing the detection zone through the stiffening means and laminate sealing means.

6. The device of claim 4 in which the stiffening means is transparent plastic.

7. The device of claim 4 in which the stiffening means are sealed to the sealing means by a sonic weld, double-sided adhesive tape, or an adhesive.

8. The device according to claim 1, further comprising means for detecting contamination with the laminate sealing means.

9. The device according to claim 1, further comprising a container for holding a sample to be assayed, wherein the laminate sealing means and assay means are secured to an interior surface of the container means.

10. The device according to claim 9, wherein the laminate sealing means is provided with means for exposing the assay means.

11. The device of claim 1 which comprises assay means for more than one analyte.

12. The device of claim 1 in which the laminate sealing means is transparent plastic tape.

13. The device of claim 1 in which the assay means comprises a material selected from the group consisting of a membrane, coated plastic, coated glass, a filter, silica gel, paper, agarose gel, polyacrylamide gel, and gelatin.

14. The device of claim 1 in which the assay means comprises a membrane formed of a material selected from the group consisting of nylon, paper, and a starch.

15. The device of claim 1 in which the assay means are attached to the laminate sealing means by an adhesive.

16. The device of claim 15 in which the adhesive is selected from the group consisting of double-sided tape and an adhesive on the sealing means.

17. An immunochromatographic assay device, comprising:

a first elongated substantially non-wettable laminate layer;

a strip member capable of absorbing and conveying a liquid sample therethrough and containing assay reagents and a detection zone for detecting the presence of an analyte in a sample, the strip member being mounted on the first layer; and a second elongated substantially non-wettable laminate layer mounted over the first layer and strip member, the first and second layer substantially sealing the strip member in an air-tight and fluid-tight manner;

wherein at least one of the first and second layers defines a transparent window aligned with the assay reagents and detection zone for observing the assay result, and first and second layers are adapted to expose the strip member to the sample.

18. The device of claim 17 in which the first or second layer is transparent plastic.

19. The device of claim 17 in which the second layer is sealed to the first layer with transparent plastic tape or a sonic weld.

20. The device of claim 17 in which the strip member is membrane formed of a material selected from the group consisting of nylon, paper, and a starch.

* * * * *